United States Patent
Phillips et al.

(10) Patent No.: US 10,492,720 B2
(45) Date of Patent: Dec. 3, 2019

(54) SYSTEM AND METHOD FOR DETERMINING SLEEP STAGE

(71) Applicant: ResMed Sensor Technologies Limited, Dublin (IE)

(72) Inventors: Paul Phillips, Down (GB); Conor Heneghan, San Jose, CA (US); Trevor Murray, Belfast (IE)

(73) Assignee: ResMed Sensor Technologies Limited (IE)

( * ) Notice: Subject to any disclaimer, the term of this patent is extended or adjusted under 35 U.S.C. 154(b) by 1068 days.

(21) Appl. No.: 14/031,553

(22) Filed: Sep. 19, 2013

(65) Prior Publication Data
US 2014/0088373 A1 Mar. 27, 2014

(30) Foreign Application Priority Data
Sep. 19, 2012 (IE) .................................. 2012/0409

(51) Int. Cl.
*A61B 5/08* (2006.01)
*A61B 5/00* (2006.01)
(Continued)

(52) U.S. Cl.
CPC .............. *A61B 5/4812* (2013.01); *A61B 5/05* (2013.01); *A61B 5/0816* (2013.01); *A61B 5/726* (2013.01);
(Continued)

(58) Field of Classification Search
CPC .. G01S 13/00; A61B 5/00; A61B 5/04; A61B 5/08; A61B 5/4806; A61B 5/4809; A61B 5/4812; A61B 5/4815; A61B 5/4818
(Continued)

(56) References Cited

U.S. PATENT DOCUMENTS 4,085,740 A 4/1978 Allen, Jr.
4,228,806 A 10/1980 Lidow
(Continued)

FOREIGN PATENT DOCUMENTS

CN 1606962 A 4/2005
JP 2000325315 A 11/2000
(Continued)

OTHER PUBLICATIONS

Burioka, Naoto, et al. "Approximate entropy of human respiratory movement during eye-closed waking and different sleep stages." Chest Journal 123.1 (2003): 80-86.*
(Continued)

*Primary Examiner* — Mallika D Fairchild
*Assistant Examiner* — Nathan A Baldwin
(74) *Attorney, Agent, or Firm* — Botos Churchill IP Law LLP

(57) ABSTRACT

Methods and apparatus monitor health by detection of sleep stage. For example, a sleep stage monitor may access sensor data signals related to bodily movement and respiration movements. At least a portion of the detected signals may be analyzed to calculate respiration variability. The respiration variability may include variability of respiration rate or variability of respiration amplitude. A processor may then determine a sleep stage based on a combination bodily movement and respiration variability. The determination of sleep stages may distinguish between deep sleep and other stages of sleep, or may differentiate between deep sleep, light sleep and REM sleep. The bodily movement and respiration movement signals may be derived from one or more sensors, such as non-invasive sensor (e.g., a non-contact radio-frequency motion sensor or a pressure sensitive mattress).

31 Claims, 9 Drawing Sheets

(51) Int. Cl.
*A61M 16/00* (2006.01)
*A61B 5/05* (2006.01)
*A61B 5/11* (2006.01)

(52) U.S. Cl.
CPC .......... *A61B 5/7264* (2013.01); *A61B 5/7278* (2013.01); *A61M 16/0069* (2014.02); *A61B 5/1118* (2013.01); *A61M 2205/3303* (2013.01); *A61M 2230/63* (2013.01)

(58) Field of Classification Search
USPC ......... 364/413; 128/630; 600/509, 300, 483; 342/22
See application file for complete search history.

(56) References Cited

U.S. PATENT DOCUMENTS

| | | | |
|---|---|---|---|
| 5,047,930 A * | 9/1991 | Martens | A61B 5/0476 128/920 |
| 5,280,791 A | 1/1994 | Lavie | |
| 5,732,696 A * | 3/1998 | Rapoport | A61B 5/0476 600/301 |
| 6,426,716 B1 | 7/2002 | McEwan | |
| 6,454,719 B1 * | 9/2002 | Greenhut | A61B 5/0816 600/481 |
| 6,804,405 B2 | 10/2004 | Christopoulos et al. | |
| 6,852,084 B1 | 2/2005 | Boesen | |
| 7,248,915 B2 | 7/2007 | Ronnholm | |
| 7,306,567 B2 | 12/2007 | Loree, IV | |
| 7,427,270 B2 | 9/2008 | Izumi et al. | |
| 7,524,279 B2 | 4/2009 | Auphan | |
| 7,608,041 B2 | 10/2009 | Sutton | |
| 7,679,545 B2 | 3/2010 | Rausch et al. | |
| 7,898,455 B2 | 3/2011 | Rosenbury | |
| 7,952,515 B2 | 5/2011 | McEwan | |
| 7,956,755 B2 | 6/2011 | Lee et al. | |
| 7,956,756 B2 | 6/2011 | Kubey et al. | |
| 8,026,840 B2 | 9/2011 | Dwelly et al. | |
| 8,096,960 B2 | 1/2012 | Loree, IV et al. | |
| 8,398,538 B2 | 3/2013 | Dothie et al. | |
| 8,428,696 B2 | 4/2013 | Foo | |
| 8,454,528 B2 | 6/2013 | Yuen et al. | |
| 8,608,655 B2 | 12/2013 | Izumi | |
| 2004/0010202 A1 | 1/2004 | Nakatani | |
| 2004/0193068 A1 * | 9/2004 | Burton | A61B 5/0476 600/544 |
| 2005/0080349 A1 | 4/2005 | Okada et al. | |
| 2006/0169282 A1 * | 8/2006 | Izumi | A61B 5/08 128/204.23 |
| 2006/0184056 A1 | 8/2006 | de Chazal et al. | |
| 2006/0293602 A1 | 12/2006 | Clark | |
| 2008/0033306 A1 * | 2/2008 | Joeken | A61B 5/029 600/485 |
| 2008/0306351 A1 | 12/2008 | Izumi | |
| 2009/0131803 A1 | 5/2009 | Heneghan et al. | |
| 2009/0203972 A1 * | 8/2009 | Heneghan | A61B 5/0507 600/301 |
| 2010/0014725 A1 | 1/2010 | Watson | |
| 2010/0152546 A1 | 6/2010 | Behan et al. | |
| 2010/0152600 A1 | 6/2010 | Droitcour | |
| 2011/0015495 A1 | 1/2011 | Dothie et al. | |
| 2011/0112425 A1 | 5/2011 | Muhlsteff et al. | |
| 2011/0124979 A1 * | 5/2011 | Heneghan | A61B 5/024 600/301 |
| 2012/0130445 A1 | 5/2012 | Lee et al. | |
| 2012/0179061 A1 | 7/2012 | Ramanan et al. | |
| 2012/0245479 A1 | 9/2012 | Ganesh et al. | |
| 2013/0006124 A1 | 1/2013 | Eyal et al. | |
| 2013/0053653 A1 | 2/2013 | Cuddihy et al. | |
| 2013/0066226 A1 | 3/2013 | Leonardo et al. | |
| 2013/0135137 A1 | 5/2013 | Mulder et al. | |
| 2013/0172770 A1 | 7/2013 | Muehlsteff | |

FOREIGN PATENT DOCUMENTS

| | | |
|---|---|---|
| JP | 2007289660 A | 11/2007 |
| JP | 2009538720 A | 11/2009 |
| JP | 2011015887 A | 1/2011 |
| JP | 2012161641 A | 8/2012 |
| WO | 2004-112606 A1 | 12/2004 |
| WO | 2007143535 A2 | 12/2007 |
| WO | 2008096307 A1 | 8/2008 |
| WO | 2008098943 A2 | 8/2008 |
| WO | 2009124297 A1 | 10/2009 |
| WO | 2010048310 A1 | 4/2010 |
| WO | 2010132850 A1 | 11/2010 |
| WO | 2011006199 A1 | 1/2011 |
| WO | 2011019091 A1 | 2/2011 |
| WO | 2012073183 A1 | 6/2012 |
| WO | 2013009988 A1 | 1/2013 |
| WO | 2013093712 A1 | 6/2013 |

OTHER PUBLICATIONS

De Chazal, Philip, et al. "Assessment of sleep/wake patterns using a non-contact biomotion sensor." Engineering in Medicine and Biology Society, 2008. EMBS 2008. 30th Annual International Conference of the IEEE. IEEE, 2008.*
Extended European Search Report for Application No. 1383835.8 dated Apr. 22, 2016.
Philip De Chazal et al., "Assessment of sleep/wake patters using a non-contract biomotion sensor", Engineering in Medicine and Biology Society, 2008. EMBS 2008, 30th Annual International Conference of the IEEE, Piscataway, NJ, Aug. 20, 2008, pp. 514-517, XP031508004.
International Search Report and Written Opinion for Application No. PCT/US2013/60652 dated Feb. 7, 2014.
Rostig, MD, Sven et al., "Nonrandom Variability of Respiration During Sleep in Healthy Humans." Sleep, vol. 28, No. 5, 2005.
U.S. Office Action dated Jan. 18, 2018 for U.S. Appl. No. 14/429,589.
U.S. Final Office Action issued in related U.S. Appl. No. 14/429,589 dated Sep. 24, 2018.

* cited by examiner

SYSTEM AND METHOD FOR DETERMINING SLEEP STAGE

CROSS-REFERENCE TO RELATED APPLICATIONS

The present application claims priority from Irish Preliminary Patent Application No. 2012/0409 filed Sep. 19, 2012, the disclosure of which is hereby incorporated herein by reference.

The invention relates to the determining of sleep stage of humans using respiration and movement signals that is useful, for example, in the assessment of sleep architecture or the quality of sleep.

Currently, human sleep stages are typically determined using a laboratory based measurement called polysomnography. In polysomnography, it is typical for several electro-encephalogram readings to be taken (EEGs are the microvolt potentials generated by brain activity that can be measured at the scalp using electrodes), in addition to other parameters such as respiration, electrocardiogram (ECG), leg movements, and electro-oculograms (EOG). Based on work originally pioneered by Rechtschaffen and Kales (R&K), it is now conventional to score human sleep in 30-second epochs, and to label these epochs using sleep stage labels.

At present, the American Academy of Sleep Medicine defines the stages of sleep as:

Wake—this is when a person is fully awake, and is characterized by a positive dominant rhythm in the occipital EEG channel (when eyes are closed), typically in the range 8-14 Hz (often referred to as alpha waves)

Stage N1—this is the lightest stage of sleep, and is characterized by the appearance of some low amplitude waves at multiple frequencies interspersed with the alpha waves for >50% of an epoch. There may also be sharp vertex waves, some slow eye movements on the EOG and/or an overall lowering of the frequency of EEG.

Stage N2—this is a slightly deeper stage of sleep, and is marked by the appearance of sleep spindles and K-complexes, on a background of mixed frequency signals. Sleep spindles are bursts of higher frequency activity (e.g. >12 Hz). K-complexes are distinct isolated bipolar waves lasting about 1-2 seconds.

Stage N3 is the deepest stage of sleep (in the original R&K classification, there were two distinct stages called Stage 3 and Stage 4). This is characterised by the appearance of slow waves (e.g., 1-2 Hz frequency) for at least 20% of an epoch.

Stage R (REM)—this is rapid eye movement sleep, and is apparent through the presence of distinct activity in the EOG signal. The EEG signals recorded are typically quite similar to Stage N1 or even wake.

An automated system from scoring polysomnogram data is described in U.S. Pat. No. 5,732,696 to Rapoport et al. The system uses a computer to look for elemental patterns in the PSG data (such as the sleep spindles described above), and then uses a probabilistic weighting to score each epoch. However this approach to the problem of determining sleep stages is limited by the technical difficulty of measurement of a full set of polysomnogramm signals, and hence is difficult and cumbersome to implement for more than a single night.

A number of systems have provided alternative solutions to the problem of determining sleep stage. One approach is to use actigraphy, in which small notion sensors (e.g., accelerometers) are worn by a user, typically in a wristwatch configuration. However, such systems have the disadvantage that they can only distinguish between sleep and wake, with poor accuracy in patients with sleep disorders.

US2006/0184056 (Heneghan et al) describes a sleep monitoring system which uses an ECG signal which is processed to determine a status for each epoch, either apneic or normal.

WO2007/143535 (Heneghan et al) describes a system for monitoring physiological signs such as sleep state by monitoring motion, breathing, and heart rate signals obtained in a non-contact fashion. A classifier model is applied to the streams of data.

A system which combines ECG and respiration methods to determine simplified sleep stage is described in US20090131803 (Heneghan et al). This combines signal characteristics derived from cardiogram and respiration signals, such as the amplitude modulation of the ECG signal and the dominant respiratory frequency in order to distinguish sleep from wakefulness.

WO2004112606 (Heneghan et al) describes a method of detecting sleep apnea using trans-cervical bioimpedance measurements.

US2011/0124979 (Heneghan et al) describes an approach to sleep monitoring using ECG and photoplethysmogram (PPG) data. These may be sensed using a Holter monitor and a pulse oximeter which are wearable in an ambulatory manner.

An approach in which cardiac R-R wave intervals are used to designate sleep as REM or non-REM is described in U.S. Pat. No. 5,280,791 to Lavie. A power spectrum of the cardiac R-R interval is calculated in order to determine the stages of sleep.

SUMMARY OF THE INVENTION

This disclosure provides various embodiments and aspects of an apparatus, system and method for determining sleep stage in a non-contact manner.

In one aspect, an apparatus, system, and method is provided for deriving the sleep stage of a human subject based solely on measurement of the bodily movement and respiration movement of the subject. The sleep stages provided can distinguish between deep sleep and all other stages of sleep, or could further differentiate between deep sleep, light sleep and REM sleep. The bodily movement and respiration movement may be obtained through a non-invasive sensor such as radio-frequency motion sensor or a pressure sensitive mattress.

Limitations of the prior art which the current invention overcomes are (a) there is no need for any direct electrical or mechanical contact with the patient, e.g., no ECG, inductance plethysmogram or bioimpedance signals are acquired, (b) there is no need for cardiac information to be acquired, sleep state estimation is performed solely on movement and respiration signals.

In one embodiment, a radio-frequency sensor unit can be placed on a bedside table near a subject's bed, while they sleep. The sensor may be range gated so that its operation can be limited to a specific distance from the sensor, providing it with a required spatial resolution. The sensor unit may communicate with a processor and display and, in one aspect, the sensor, processor, and display may be physically implemented in the same unit. The processor may be used to extract information about breathing and motion, and higher order information such as the sleep stage. A display may be configured to provide feedback to the user, typically at the end of the night, such as displaying a sequence of the overnight sleep stages. Feedback can also be provided real time such that to allow using the presence of sleep to control environmental factors such as the ambient temperature, the ambient light level, the ambient noise or ambient odour. The feedback could also be used to control electronic devices such as radios, televisions or other entertainment devices. In one aspect, a complete system may include one or more of the following: A motion sensor (for detection of general bodily movement and respiration); a processing capability (to derive signals directly related to breathing and motion, and hence to derive sleep stage); a display capability (to provide visual feedback); a lighting and/or light controlling capability (to alter room light), an auditory capability (to provide acoustic feedback, e.g., a white noise generator whose amplitude varies with sleep stage); and/or a communications capability (wired or wireless) to transmit acquired data to a separate unit. The same or separate unit may be configured to carry out the processing, display, lighting and auditory functions mentioned above. The separate unit could be a local device such as a cellular phone or tablet computer, or it could be a remote computer.

In one or more embodiments, the disclosed system for measuring the respiration and movement signal comprises one or more sensors configured to receive a reflected radio-frequency signal off a living subject, a processor configured to analyze the reflected signal to determine a measurement of movement and respiration, and hence sleep stage; and a display arranged to provide selected information relating to breathing, movement and sleep stage to a user of the system. The system may further comprise a transmitter that generates the radio frequency signals that are reflected off the living subject, and the power levels emitted by the system are safe for continuous use with humans.

In another embodiment, a method for measuring, analyzing, and displaying respiration, cardiac activity, and bodily movement includes receiving radio-frequency signals reflected from a human subject; analyzing the reflected signals to produce measurements relating to movement and respiration, and hence sleep stage; and providing selected information to a user of the system.

In one aspect, the invention provides a method for classifying sleep stages of a subject, the method comprising:
detecting one or more signals related to bodily movement and respiration movements of the subject; and
analyzing at least a portion of the detected signals to calculate the variability of the respiration rate and/or respiration amplitude; and
combining the respiration variability with the bodily movement detection to determine sleep stage.

In one embodiment, the analysis determines respiration rate and respiration amplitude. Preferably, the method includes analyzing the entire detected signal to classify the sleep stages of the subject. Preferably, the detection of the one or more signals is performed in a non-contact manner.

In one embodiment, the method comprises the detection of the presence or absence of a person. Preferably, the analysis comprises a simplified sleep staging calculation in which the outputs are sleep or awake only. In one embodiment, detected signals are processed to estimate a respiratory rate of the subject. In one embodiment, detected signals are processed to estimate the respiratory amplitude of the subject. Preferably, an estimate of the respiratory rate is made on an epoch basis. In one embodiment, the analysis includes choosing a respiration stability threshold value depending on a comparison of the variation in amplitude of the measured respiratory signal with an amplitude threshold value. Preferably, the analysis includes choosing a respiration rate stability threshold value depending on a comparison of the variability of the measured respiratory rate signal with a threshold value.

In one embodiment, the analysis comprises calculating a respiration rate range for each of a number of epochs, based on the minimum and the maximum values of the respiration rates of each of the respective epochs. Preferably, the method comprises:
a. comparing the calculated respiration range with a chosen stability threshold value for the epoch; and
b. classifying the epoch as a deep sleep if the calculated respiration range is smaller than the chosen stability threshold, or otherwise classifying the epoch as light sleep.

In one embodiment, a light sleep epoch is encountered, the sequence length of prior deep sleep epochs and, if the number of preceding epochs of deep sleep epochs encountered since the last light sleep epoch is less than a predetermined number, reclassifying these epoch as light sleep. In one embodiment, the predetermined number is five.

In one embodiment, the method comprises classifying periods of sleep as either deep sleep or REM sleep on the basis of the variation of the breathing rate during the period.

In one embodiment, the method includes classifying a period as either a deep sleep or a REM sleep period, based on whether a combination of features derived from spectral analysis and approximate entropy analysis for the period is smaller or larger, respectively, than a threshold value. In one embodiment, non-contact radiation-based sensors are used, and the analysis provides quadrature signals I and Q which represent the detected movement observed from positions 90° apart in the phase space of a transmitter.

In one embodiment, the analysis uses respiration rate variability and respiration amplitude variability to determine sleep stage. In one embodiment, the analysis uses variability of the respiration rate and amplitude to distinguish REM sleep, in which a period of relatively high variation of the breathing rate is considered as an indication of an REM sleep period, and a period of relatively low variation of the breathing rate is considered to be associated with a state of deep sleep. In one embodiment, the analysis comprises assessing the variability of a time series using the approximate entropy, which assumes lower values for predictable time-series, and higher values as the time-sequence becomes more variable. Preferably, the analysis provides a continuous respiration rate and respiration amplitude estimate, and the respiration rate is then fed into two processing blocks in segments, in which a block will output a single number for an epoch which is the approximate entropy of that segment of the signal.

In another aspect, the invention provides a system for classifying sleep stages of a subject, the system comprising:
one or more sensors configured to detect one or more signals which relate to bodily movement and respiration related movements; and a processor configured to analyze at least a portion of the detected signals to calculate the variability of the respiration rate and/or respiration amplitude; and to combine the respiration variability with the bodily movement detection to determine sleep stage.

In one embodiment, at least one of the one or more sensors is a non-contact sensor. In one embodiment, the at least one non contact sensor is a radio frequency based sensor. In one embodiment, the at least one non-contact radio sensor is range gated.

In a further aspect, the invention provides a computer readable medium comprising software code adapted to perform the steps of a method as defined above in any embodiment, when executing on a digital processor.

BRIEF DESCRIPTION OF THE DRAWINGS

Embodiments of the disclosure will now be described with reference to the accompanying drawings in which:

FIG. 7 shows analysis of the power spectral density estimate of the respiration rate signal, in which FIG. 7(a) shows a linear fit to the log-log plot of the PSD, and FIG. 7(b) shows the power contained within various spectral bands;

DETAILED DESCRIPTION

Figure 1:
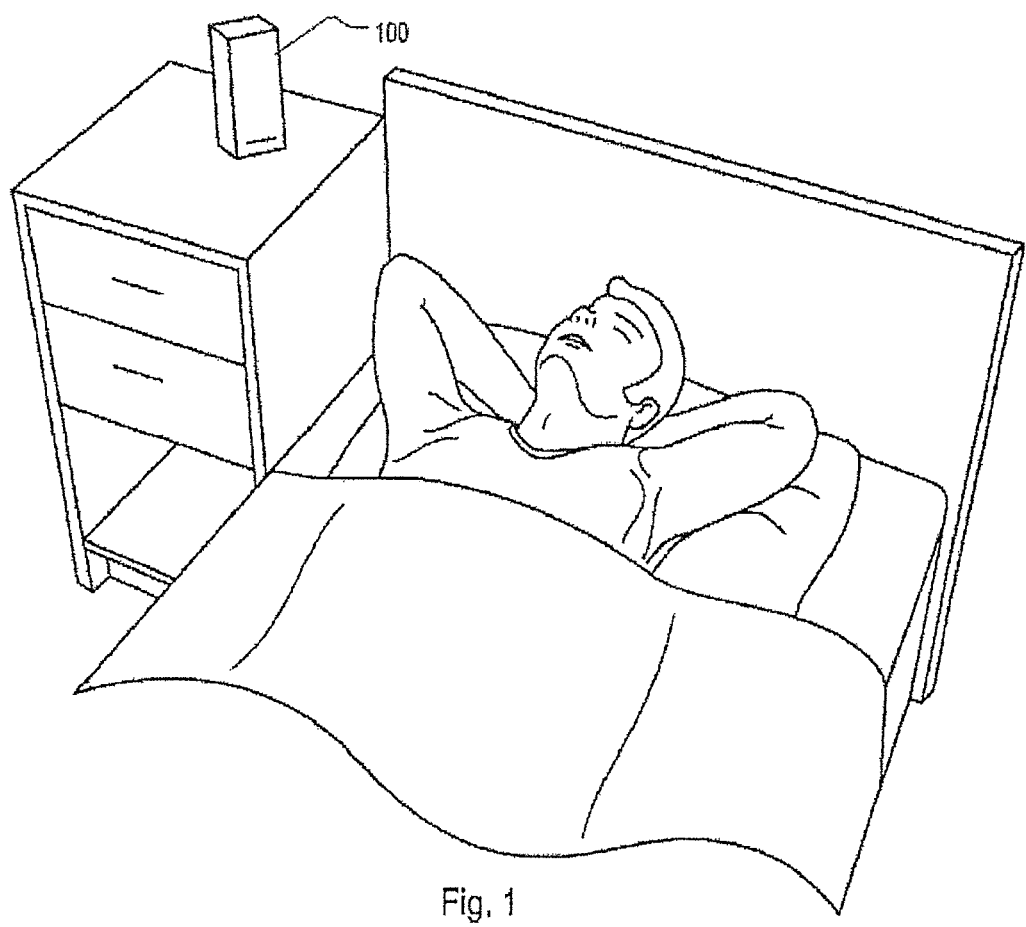
FIG. 1 is a diagram illustrating a schematic of how a system of an embodiment might be used in assessment of sleep stage, wherein the system is placed at a bedside table and acquires measurements relating to the movement and breathing of the subject.

FIG. 1 is a diagram illustrating a use case scenario for the system. The sensor, processing and display means are all embodied in one unit, 100. In this case, the sensing modality is totally non-contact, and operates through the means of transmitting electromagnetic waves towards the subject. The device is configured to be sensitive to movement within a distance of 1.2 m, but does not detect movement from more distant objects. This ensures that interference from a second person in the bed or nearby moving objects such as fans is minimised.

In one embodiment the radiation used is in the microwave range, in which the sensor is of the type described in U.S. Pat. No. 6,426,716, the full contents of which are incorporated herein by reference.

In another embodiment, the radiation is in the form of narrow virtual transmit pulses synthesized by differencing long-duration staggered pulse repetition interval (PRI) transmit pulses. Such a sensor is described in U.S. Pat. No. 7,952,515, the full contents of which are incorporated herein by reference.

In the cases where these radio-frequency based sensors are used, they will produce so-called quadrature signals I and Q which represent the detected movement observed from positions 90° apart in the phase space of the transmitter. An advantage of this approach is that it can help determine the direction of movement, and also smooth out the overall sensitivity of the system.

Figure 2:
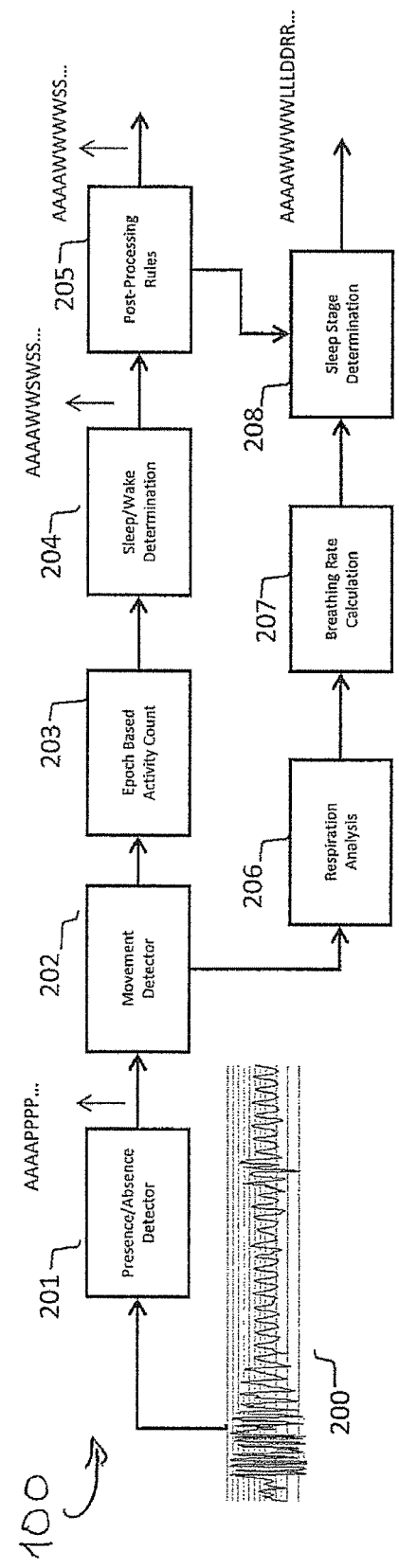
FIG. 2 provides a schematic representation of the overall processing of the movement and respiratory signals, in which various levels of outputs are possible, namely, an indicator of whether a subject is present or absent, an indication of whether a person is asleep or awake, or an indication of the sleep stage.

FIG. 2 shows the overall process and processing means used by the system. The sensor acquires at least one signal 200 which represents the movement of the body. In general, this movement will include components due to breathing effort and non-respiratory movements such as turning over, twitching, or adjusting position etc. Such signals could be provided by a radio frequency bio-motion sensor, but could also be acquired by one or more respiratory inductance plethysmography, by pressure sensors embedded in a mattress, by a bioimpedance measurement system, by an end-tidal $CO_2$ respiratory monitor, by an ultrasonic sensor, or by an optical sensor.

The first step of processing is to determine whether a person is present or absent using the presence-absence detector 201. The means for determining presence or absence can be through measurement of the amplitude of the signal (e.g., the root mean square value of the signal) or could involve more complex processing such as determining the spectral content of the signal relative to the expected noise floor of the sensor(s). In one embodiment the processing is performed in a manner as described in WO2007/143535, the full contents of which are incorporated herein by reference. In another embodiment, periods of movement can be determined by taking the arctangent of the quadrature I and Q signals mentioned above. In this case, the resulting signal will be related directly to the displacement of the object being observed, if normalization and phase unwrapping is correctly carried out. Given the displacement signal, presence-absence can then be determined by seeing if the energy in the displacement signal is greater than a set threshold.

The output of the presence-absence detector stage of processing will be a sequence of epoch labels such as "AAAAPPP", where "A" is absent and "P" is present, and an epoch may represent a fixed period of time such as 30 seconds. The signal is then fed to a movement detector 202 which determines whether movement is present (typically on a shorter time scale such as 1 second). A means for determining movement may be through counting level-crossings of the signal, or by measuring the high frequency content of the signal. The detailed methodology of such measurement is described in WO2007/143535.

Each second can then be associated with movement or non-movement. The outcomes of each 1-second movement detector can be combined into an epoch-based activity count 203. For example, if an epoch is 30 seconds, and each 1-second period within an epoch has movement, then the overall activity count for that epoch is 30. The amplitude of the movement detected can also be included in the activity count metric. Based on the activity count, the sleep wake determination means 204 assigns labels based on the level of the activity count (for example, an activity count greater than 20 may be considered as a wake epoch). The activity counts of surrounding epochs may also be considered in making this determination. The post-processing rules 205 can be further used to enhance the accuracy of the sleep/wake determination, by for example removing single isolated epochs of SLEEP surrounded by WAKE. The overall output of the post-processing rules will be a sequence of labels (which can combine the information from the presence/.absence detector) which may look like; "AAAAWW-WWWSSSSSS", where "A" is absent, "W" is wake, and "S" is sleep.

In parallel to determining the sleep/wake status, further processing is used to determine the sleep stage. The respiration analysis block 206 is used to enhance the respiration signal, for example by filtering the raw signal using a low pass filter. Using the information from the movement detector 202, the respiration analysis may also label certain sections of signal as being too heavily contained by movement signals to provide reliable respiration rate estimates. The respiration rate calculation 207 is used to determine the breathing rate of the person, for example in breaths/minute or in Hz. The respiration rate can be calculated using a power spectral density estimate, or by using an auto-regressive model of the signal. The detailed methodology of such calculation is described in WO2007/143535. The calculation provides estimates of the respiration rate for example on a per-epoch basis, or alternatively on a shorter time scale (e.g., once/second). These respiration rates are provided to the sleep stage determination means 208 which uses the respiration rates to determine sleep stage. In one embodiment, the respiration rate is used to distinguish deep sleep (Stage N3) from all other stages of sleep (N1, N2 and REM). The relative amplitude of respiration can also be determined.

Figure 3:
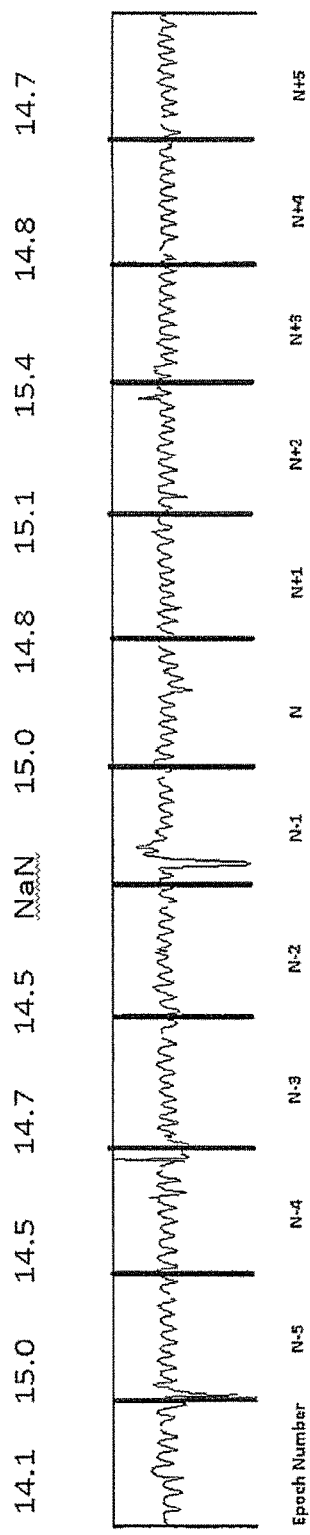
FIG. 3 shows how a sensor signal can be divided into epochs, with each epoch associated with a respiration rate.

For explanatory purposes, FIG. 3 shows the output of the respiration rate block 207 from FIG. 2. In this, it is shown how the signal can be considered in epochs (30 seconds in this case) and how each epoch could have a single respiration rate associated with it. This respiration rate is the rate associated with the maximum power spectral density of the epoch. The epochs can be labelled sequentially as Epoch N, N+1, etc. For example, in this case Epoch N−5 might have a rate of 15 breaths/minute, N−4 might be 14.5 breaths/min, etc. Also, as an illustrative point, the respiration analysis block 206 might deem Epoch N−1 to have such large movement that it cannot supply a reliable respiration rate. In such cases, the epoch rate might be labelled as "Unavailable" or "Not a Number".

Figure 4:
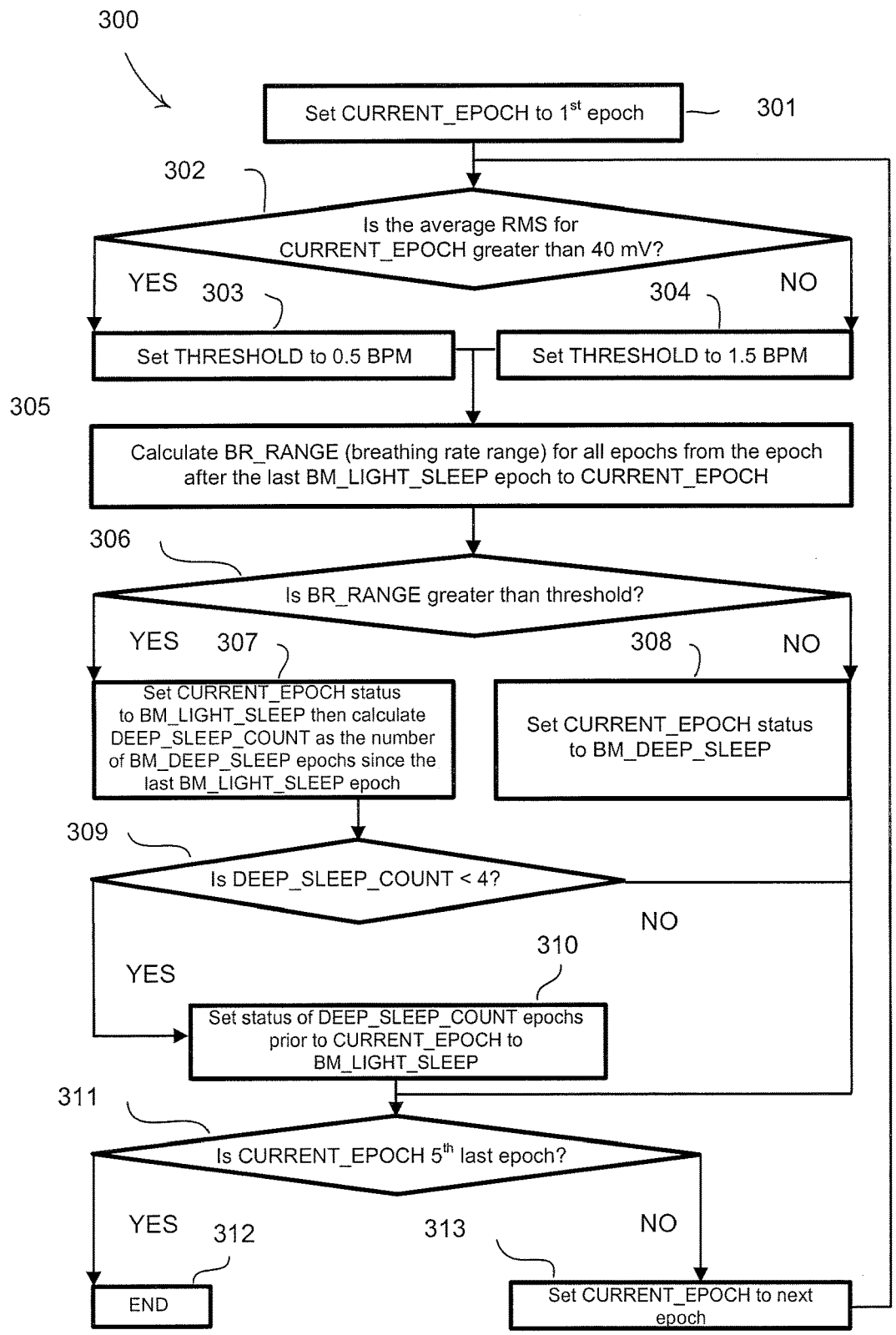
FIG. 4 provides a flow diagram of the processing used to determine whether a person is in deep sleep (Stage N3 described above)

FIG. 4 shows in more detail a specific embodiment of a sleep determination means 208 from FIG. 2. The general principle of operation is to determine sequence of epochs where the respiration rate is quite stable. The set of SLEEP/WAKE labels for an entire recording is provided to the algorithm. The algorithm is initiated by assigning (301) the variable "CURRENT EPOCH" to be the first epoch in the series.

The system decides whether the CURRENT_EPOCH has a high amplitude signal (representing good signal quality). If the signal quality is good, then the algorithm can be very confident in the estimate of respiration rate. In this embodiment, an average signal amplitude of >40 mV (steps 302, 303, 304) is indicative of a high quality signal, and in this case we will use a stability threshold of 0.5 breaths/minute. For situations where the signal is lower quality we use a more tolerant limit of 1.5 breaths/minute for the allowed respiration rate variability.

The algorithm then calculates (305-308) the respiration rate range by finding the minimum and maximum value of all the epochs' respiration rates between the CURRENT_EPOCH and the last epoch labelled as LIGHT_SLEEP. For example, if the last LIGHT_SLEEP was epoch N−6 with a rate of 14.2 BPM, and the epochs [N−5, N−4, . . . , N] had rates=[14.4, 14.8, 15.1, 14.9, 14.7, 14.6], then the breathing rate range is (15.1−14.4)=0.7 breaths/minute. If this BREATHING_RATE_RANGE is less than the stability threshold, then the current epoch is labelled as deep sleep (308). Alternatively, if the BREATHING_RATE_RANGE is larger than the stability threshold, then the current epoch is labelled as light sleep (307). Since very short sequences of DEEP_SLEEP are relatively uncommon, the algorithm also excludes (309, 310) cases where there is a run of four or less deep sleep epochs. This is done by checking the current sequence length of the DEEP_SLEEP prior epochs when a LIGHT_SLEEP epoch is encountered. If there are four or less preceding epochs of DEEP_SLEEP encountered since the last LIGHT_SLEEP epoch, these epoch labels are converted (310) to LIGHT_SLEEP. Since this condition makes it impossible to finish with DEEP_SLEEP count of less than 5, in such a case by default the algorithm accepts (311-313) the WAKE or SLEEP labels for the last four epochs (with SLEEP automatically treated as LIGHT_SLEEP).

As a further refinement of the embodiment described above, the stability threshold for "stable breathing" can be refined on a per-subject basis. For example, the default analysis may use a stability threshold of 0.5 breaths/minute, but if this threshold produces physiologically unreasonable values for deep sleep duration (e.g., >40% or less <5%), the threshold could be adaptively modified to a more suitable value.

Figure 5:
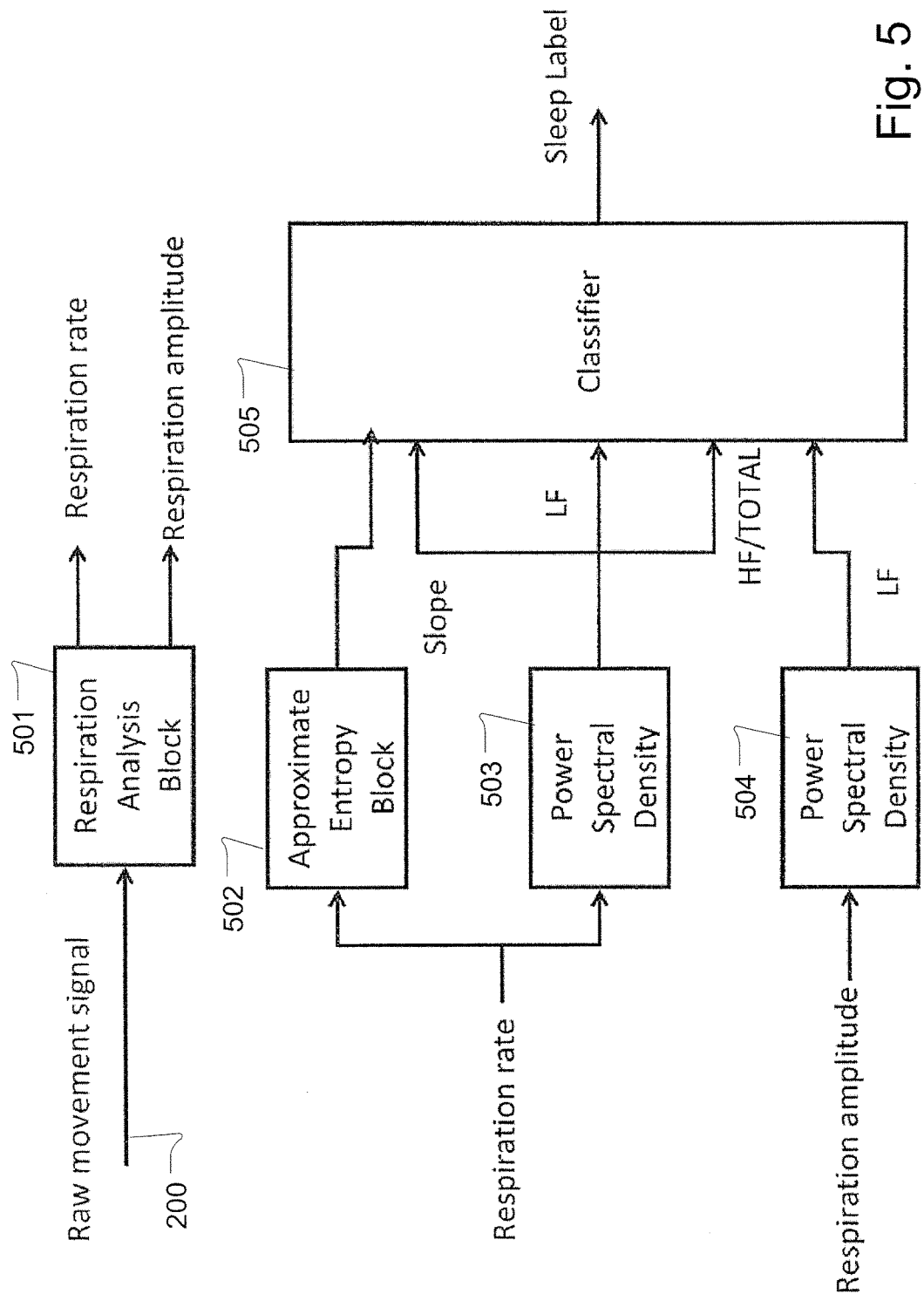
FIG. 5 shows the classification of a period of sleep on the basis of the variation of the respiration rate and amplitude signals during the period.

An alternative embodiment which uses respiration rate variability and amplitude to determine sleep stage is shown in FIG. 5. This is based on the observation that the variability of the respiration rate and amplitude can be used to distinguish REM sleep. A period of relatively high variation of the breathing rate is considered as an indication of a REM sleep period. A period of relatively low variation of the breathing rate is considered to be associated with a state of deep sleep. One embodiment for assessing the variability of a time series is the approximate entropy. The approximate entropy assumes lower values for predictable time-series, and higher values as the time-sequence becomes more variable. In this embodiment, the raw signal 200 is fed to a respiration analysis block. This respiration analysis block outputs a continuous respiration rate and respiration amplitude estimate (pictured in FIG. 6), e.g. on a 1-second timescale. The respiration rate is then fed into two processing blocks in segments (typically of duration 5 minutes, i.e. 300 samples of the respiration rate will be passed into the blocks labelled "Approximate Entropy Block" 502 and the "Power Spectral Density" 503. The approximate entropy is a technique used to assess the predictability of a signal (i.e. variability) and is described in the Wikipedia.org article titled "Approximate entropy." The block will output a single number for the 5 minute epoch entered, which is the approximate entropy of that section of the signal. For example, we can calculate the approximate entropy of five-minute segments of respiration rate, using parameters of $m=2$ and $m=3$ for the embedding dimensions, and a value of $r$ equal to 0.2 The power spectral density block will estimate the power spectral density of the respiration rate, using a technique such as Welch's averaged periodogram. The PSD estimate will then provide three measurements: the slope of the PSD, the normalised high frequency power of the respiration rate variability and the low-frequency power of the respiration rate variability. The power spectral density block will be applied to the respiration amplitude signal also, and will output a Low Frequency (LF) power estimate. The values calculated from the processing blocks (502, 503 and 504) will be fed to a classifier which will combine them to produce a number which is then used to estimate a Sleep Label (drawn from N1, N2, N3, REM or W).

An alternate embodiment to power spectral density which can also capture the short-term and long-term correlations of the respiration rate is to use detrended fluctuation analysis, a description of which can be found in "Establishing the relation between detrended fluctuation analysis and power spectral density analysis for stochastic processes," Phys Rev E Stat Phys Plasmas Fluids Relat Interdiscip Topics. 2000 November; 62(5 Pt A):6103-10, by Heneghan and McDarby.

Figure 6:
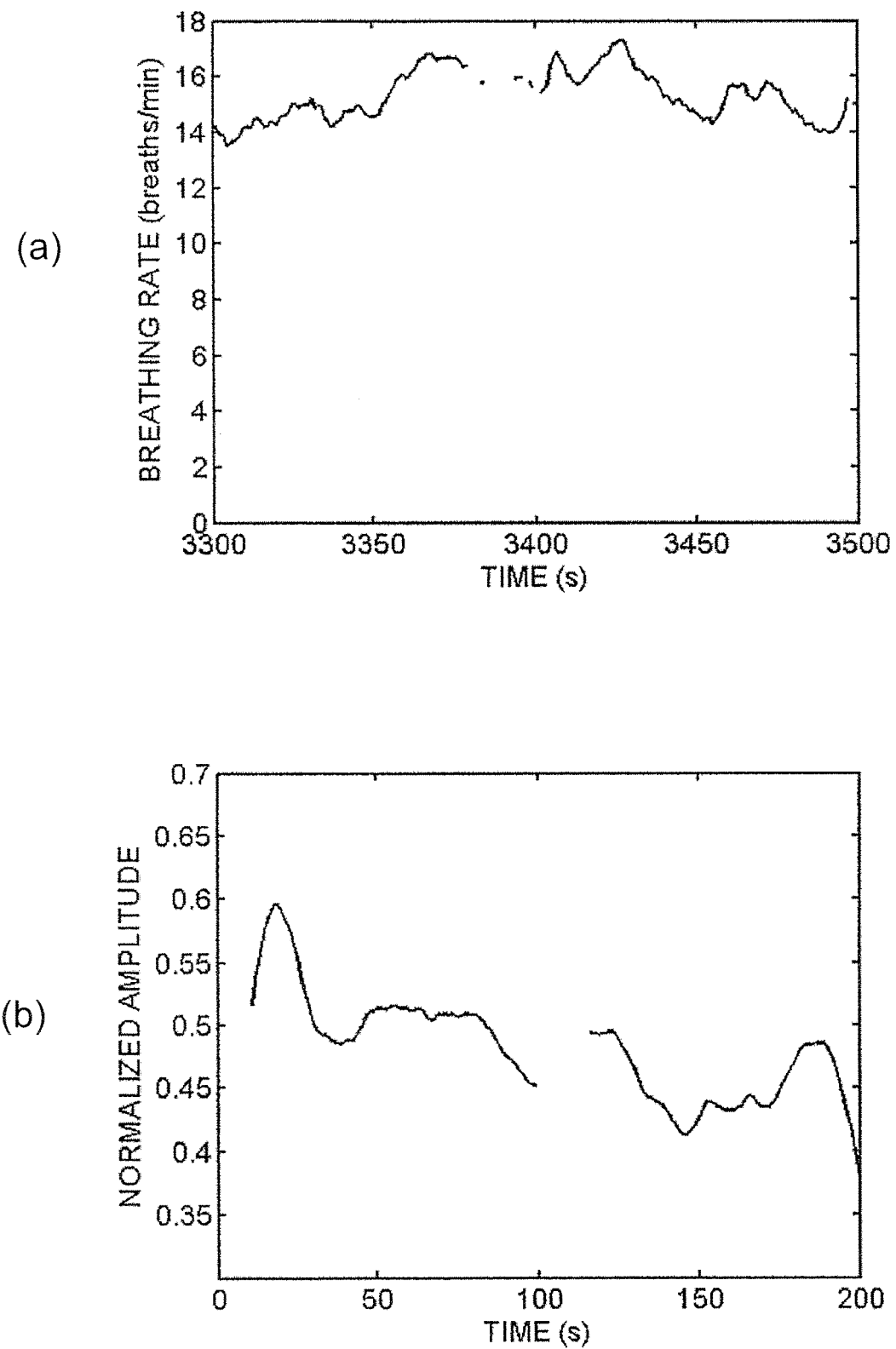
FIG. 6 shows an example of (a) a respiration rate signal and (b) a normalized respiration amplitude signal as a function of time.

FIG. 6 illustrates an example of the respiration rate signal and the normalized respiration amplitude signals which are used in FIG. 5. The respiration rate signal is shown in FIG. 6(a); there are periods of missing signals where the signal quality is insufficient for a reliable respiration rate estimate. The normalized respiration amplitude signal is shown in FIG. 6(b); there are periods of missing signals where the signal quality is insufficient for a reliable respiration amplitude estimate. The respiration rate amplitude signal can be obtained by filtering the raw signal to the respiration rate range first and then applying a Hilbert transform, or it could be taken from the amplitude of the peak in respiration rate estimation.

Figure 7:
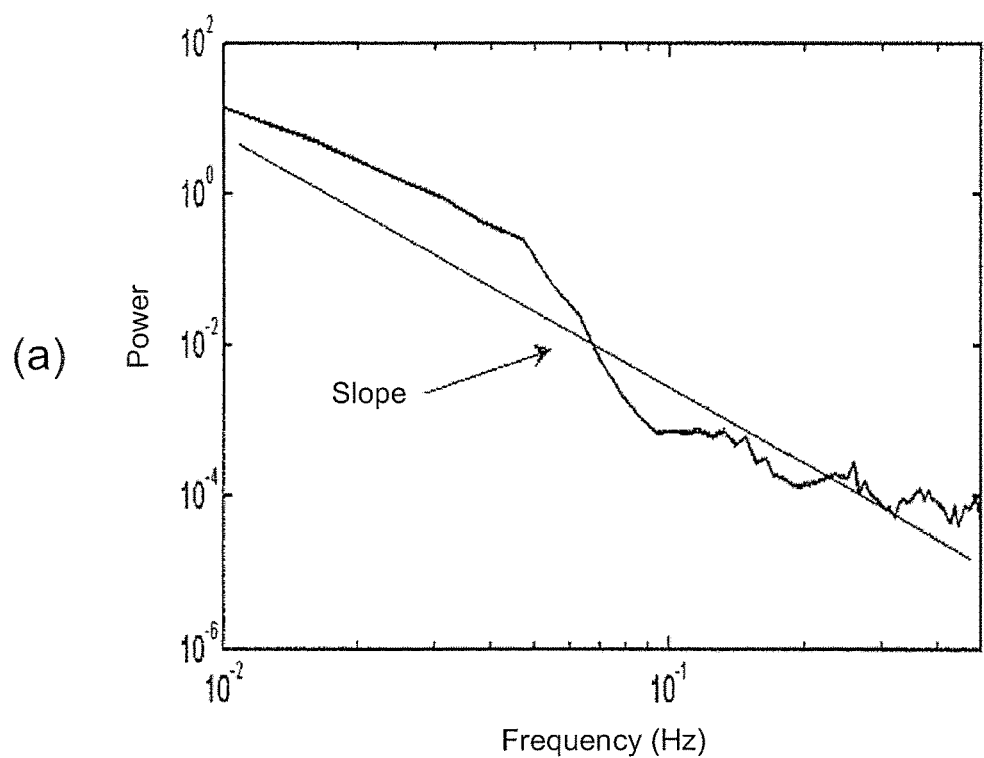
Figure 7:
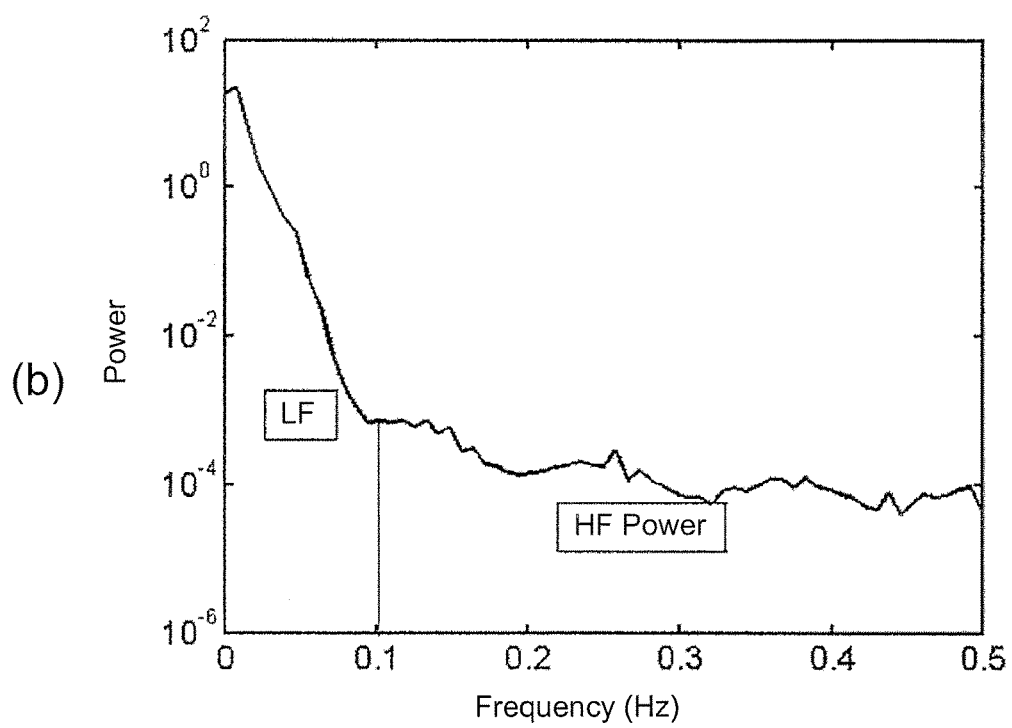

FIG. 7 shows some of the intermediate processing steps in FIG. 5. In FIG. 7(a), we illustrate the power spectral density estimate of a segment of 5-minutes of respiration rate, plotted on a log-log plot. A line is then fitted to the slope, and the slope of this line is an output from the processing block. This is based on physiological observations of the long-term and short term control of respiration variability (see Rostig S; Kantelhardt J W; Penzel T et al. "Nonrandom variability of respiration during sleep in healthy humans." SLEEP 2005; 28(4):411-17.) In FIG. 7(b), we show the power spectral density of five minutes of respiration rate shown on a semi-log scale. Power is represented at different frequencies. The "HIGH FREQUENCY—HF" power of the respiration rate variability can be considered as the integral of the PSD from 0.1 to 0.5 Hz. This can be normalised by dividing by the entire power of the signal. The "LOW-FREQUENCY LF" power can be defined as the power between 0 and 0.1 Hz.

Figure 8:
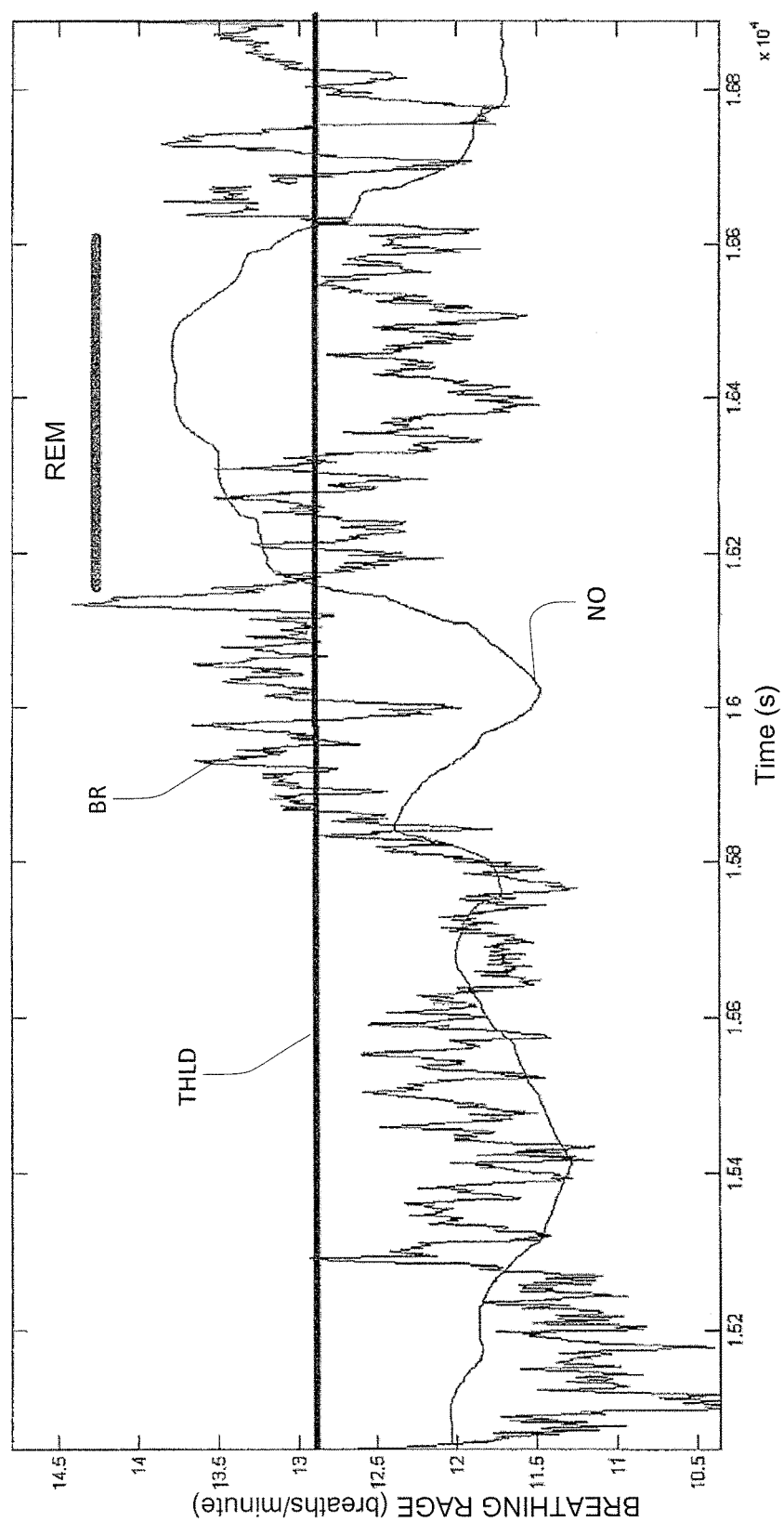
FIG. 8 shows a plot of the respiration rate over a period of time, and superimposes the output of the sleep stage classifier shown in FIG. 5—it indicates how this could then be mapped to a REM sleep stage.

A schematic representation of how a scaled version of the output of the Classifier block may vary is shown in FIG. 8 as a smoother uninterrupted line. The breathing rate is visualised by the more variable line in the image. A threshold value may be used for classifying the sleep during a specific period. Such a value is illustrated by the straight horizontal line crossing the breathing rate axis slightly below the value of 13 breaths per minute. If the classifier block output for the period is above the predetermined threshold value, the respective period may be classified as a REM sleep period. Alternatively, if the classifier block output for the period is below the predetermined threshold value, the respective period may be classified as period of deep sleep. This is an alternative way of classifying a period as a deep sleep to that described with reference to FIG. 4

Figure 9:
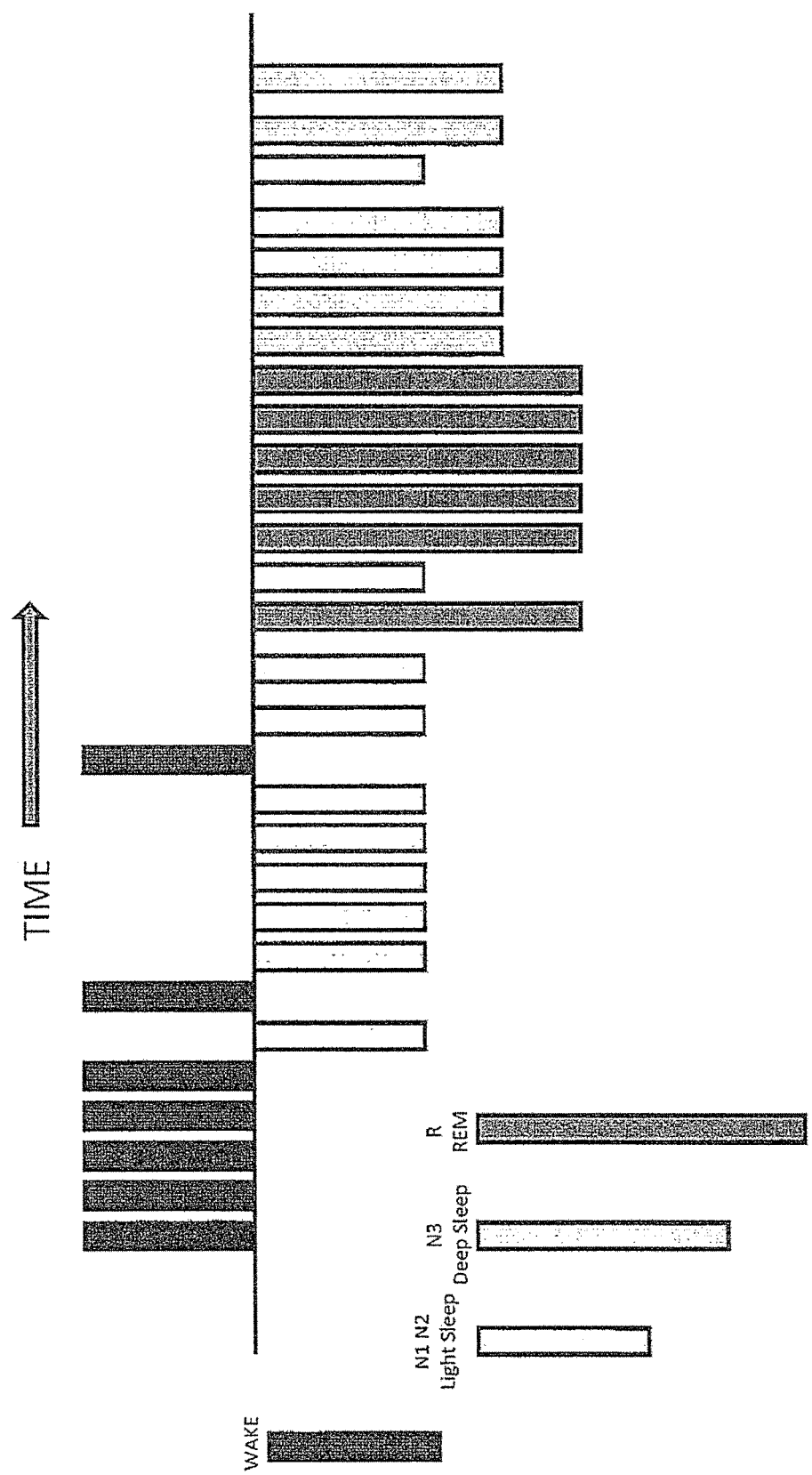
FIG. 9 s a flow diagram showing how the system assigns data to epochs.

FIG. 9 shows a means for illustrating the time course of the sleep stages to a user by using color-coded vertical bars. Bars extending above the main axis indicate a state of wake. Bars extending below the axis indicate a sleep state. The amplitude of the bars corresponds to the stage of sleep, the shortest bars indicating light sleep, the medium length bars indicating deep sleep and the longest bars indicating a REM sleep.

STATEMENT OF INDUSTRIAL APPLICABILITY

This disclosure has application in the field of sleep research and in providing quality-of-life metrics to individual users.

The invention claimed is:

1. A method for classifying sleep stages of a subject, the method comprising:

detecting, by one or more sensors, one or more signals related to respiration movement of the subject;
deriving, by one or more processors, in a respiration analysis block, at least a respiration rate signal from the one or more signals related to respiration movement;
applying to a power spectral density block, the respiration rate signal from the respiration analysis block;
analyzing, by the one or more processors, in the power spectral density block, at least the derived respiration rate signal to calculate at least one feature, the at least one feature comprising power spectral density of the respiration rate signal;
combining, by the one or more processors, a plurality of features calculated by the one or more processors, the plurality of features including one or more measurements from the power spectral density of the respiration rate signal, to determine sleep stage in a classifier, wherein the one or more measurements includes a fitted slope of at least one estimate of the power spectral density of the respiration rate signal; and
determining, with the classifier, the sleep stage based on the power spectral density of the respiration rate signal.

2. The method as claimed in claim 1, further comprising deriving, in the respiration analysis block, a respiration amplitude signal from the one or more signals related to respiration movement.

3. The method of claim 2, further comprising applying, to an approximate entropy block, the respiration rate signal to produce an approximate entropy value for a section of the respiration rate signal, and wherein the approximate entropy value is a feature of the plurality of features.

4. The method of claim 2, wherein the analyzing includes choosing a respiration stability threshold value depending on a comparison of a respiration amplitude with an amplitude threshold value.

5. The method of claim 2, wherein the analyzing comprises calculating a respiration rate range for each of a number of epochs, based on minimum and maximum values of respiration rates of each of the respective epochs.

6. The method of claim 5, the method comprising:
a. comparing, by the one or more processors, the calculated respiration rate range with a chosen stability threshold value for the epoch; and
b. classifying, by the one or more processors, the epoch as a deep sleep if the calculated respiration rate range is smaller than the chosen stability threshold value, or otherwise classifying the epoch as light sleep.

7. The method of claim 6, the method comprising counting, when a light sleep epoch is encountered, a sequence length of prior deep sleep epochs and, if a number of preceding epochs of deep sleep epochs encountered since a last light sleep epoch is less than a predetermined number, reclassifying these epoch as light sleep.

8. The method of claim 7, wherein the predetermined number is five.

9. The method of claim 2, wherein the method comprises classifying, by the one or more processors, periods of sleep as either deep sleep or REM sleep on a basis of a variation of the respiration rate signal during the period.

10. The method of claim 1, wherein the detection of the one or more signals is performed in a non-contact manner.

11. The method of claim 1, the method comprising detection of presence or absence of a person.

12. The method of claim 1, wherein the analyzing comprises a simplified sleep staging calculation in which outputs are sleep or awake only.

13. The method of claim 1, wherein the analyzing includes choosing a respiration rate stability threshold value depending on a comparison of a respiratory rate with a threshold value.

14. The method of claim 1, wherein the method includes classifying a period as either a deep sleep or a REM sleep period, based on whether a combination of features derived from spectral analysis and approximate entropy analysis for the period is smaller or larger, respectively, than a threshold value.

15. The method of claim 1, wherein the analyzing includes choosing a respiration stability threshold value depending on a quality of the one or more detected signals.

16. The method of claim 15, wherein the quality of the one or more detected signals is determined based on an average signal amplitude.

17. The method as claimed in claim 1, wherein the method includes:
deriving, by the one or more processors, a respiration amplitude signal from the one or more signals related to the respiration movement of the subject; and
analyzing, by the one or more processors, the derived respiration amplitude signal to calculate the plurality of features.

18. The method of claim 17, wherein the one or more measurements further comprises, a normalised high frequency power of the respiration rate signal, and a low-frequency power of the respiration rate signal, the normalized high frequency power concerning first one or more frequencies and the low-frequency power concerning second one or more frequencies, wherein the first one or more frequencies are higher than the second one or more frequencies.

19. The method of claim 17, wherein the plurality of features are derived based on a variability of at least one of the respiration amplitude signal and the respiration rate signal.

20. The method as claimed in claim 19, wherein the analyzing uses the variability of the respiration rate signal to distinguish REM sleep, in which a period of relatively high variation of the respiration rate signal is considered as an indication of an REM sleep period, and a period of relatively low variation of the respiration rate signal is considered to be associated with a state of deep sleep.

21. The method as claimed in claim 19, wherein the analyzing comprises assessing the variability of the respiration rate signal of a time series using an approximate entropy, which assumes lower values for predictable time series, and higher values as the time series becomes more variable.

22. The method of claim 19, wherein the one or more sensors include a non-contact radiation-based sensor that are used to detect one or more signals related to bodily movement measurements of the subject and wherein the one or more processors are configured to combine at least one of the variability of the respiration amplitude signal and the variability of the respiration rate signal with the bodily movement measurements to determine sleep stage.

23. The method of claim 22, wherein the detected one or more signals are quadrature signals I and Q which represent detected bodily movement observed from positions 90° apart in a phase space of a transmitter.

24. The method as claimed in claim 17, wherein the respiration analysis block provides a continuous respiration rate signal and continuous respiration amplitude signal, and the respiration rate signal and the respiration amplitude signal are processed in segments, and wherein a processing block will output a single number for an epoch which is an approximate entropy of that segment of the respiration rate signal.

25. The method of claim 1, wherein the plurality of features are derived based on a variability of the respiration amplitude signal.

26. The method of claim 1 wherein the respiration rate signal comprises a time signal of values wherein each of the values represents a breath-per-minute.

27. The method of claim 1, wherein the one or more measurements further comprises a normalised high frequency power of the respiration rate signal, and a low-frequency power of the respiration rate signal, the normalized high frequency power concerning first one or more frequencies and the low-frequency power concerning second one or more frequencies, wherein the first one or more frequencies are higher than the second one or more frequencies.

28. A non-transitory computer readable medium comprising software code adapted to perform a method of claim 1 when executing on a digital processor.

29. A system for classifying sleep stages of a subject, the system comprising:
one or more sensors configured to detect one or more signals which relate to respiration movements of the subject and to bodily movement of the subject; and
one or more processors configured to, for a selected epoch:
derive a respiration rate signal in a respiration analysis block from the one or more signals wherein the respiration rate signal varies over time;
apply to a power spectral density block, the respiration rate signal from the respiration analysis block;
calculate, in the power spectral density block, at least one feature, the at least one feature comprising power spectral density of the respiration rate signal;
combine a plurality of calculated features, the plurality of calculated features including one or more measurements from the power spectral density of the respiration rate signal wherein the one or more measurements includes a fitted slope of at least one estimate of the power spectral density of the respiration rate signal; and
determine, in a classifier, sleep stage for the selected epoch with the plurality of calculated features including the one or more measurements from the power spectral density of the respiration rate signal.

30. The system of claim 29 wherein at least one of the one or more sensors is a non-contact, radio-frequency, and range-gated sensor.

31. The system of claim 29 wherein the one or more measurements further comprises a normalised high frequency power of the respiration rate signal, and a low-frequency power of the respiration rate signal, the normalized high frequency power concerning first one or more frequencies and the low-frequency power concerning second one or more frequencies, wherein the first one or more frequencies are higher than the second one or more frequencies.

* * * * *